United States Patent [19]
Askham

[11] Patent Number: 5,744,656
[45] Date of Patent: Apr. 28, 1998

[54] CONVERSION OF HEXAFLUOROBENZENE TO BROMOPENTAFLUOROBENZENE

[75] Inventor: Fredric Askham, Loveland, Colo.

[73] Assignee: Boulder Scientific Company, Mead, Colo.

[21] Appl. No.: 736,655

[22] Filed: Oct. 25, 1996

[51] Int. Cl.$^6$ .................................................. C07C 22/00
[52] U.S. Cl. ............................................ 570/147; 570/143
[58] Field of Search ..................................... 570/147, 143

[56] References Cited

U.S. PATENT DOCUMENTS 3,429,935  2/1969  Wall et al. ............................. 570/147
5,233,074  8/1993  Lal ..................................... 570/143 X

*Primary Examiner*—Paul F. Shaver
*Attorney, Agent, or Firm*—Edward S. Irons

[57] ABSTRACT

A method for producing tetrakis (pentafluorophenyl) borates is described. Hexafluorobenzene is converted to bromopentafluorobenzene which may be isolated and then reacted with an alkyl lithium to produce pentafluorophenyl lithium which in turn is reacted directly with an appropriate reagent to produce the desired borate.

9 Claims, No Drawings

CONVERSION OF HEXAFLUOROBENZENE TO BROMOPENTAFLUOROBENZENE

BACKGROUND OF THE INVENTION

This invention relates to the conversion of hexafluorobenzene to bromopentafluorobenzene and to the use of the bromopentafluorobenzene so produced as a source of a pentafluorophenyl group in medical drugs or boron compounds useful as olefin polymerization co-catalysts such as tris(pentafluorophenyl) borane and tetrakis (pentafluorophenyl) borate derivatives. See, generally, U.S. Pat. Nos. 5,362,423 and 5,470,993. Bromopentafluorobenzene is very expensive and in short supply. Hexafluorobenzene, however, is readily available. Accordingly, a need exists for a cost effective method to convert hexafluorobenzene to bromopentafluorobenzene.

SUMMARY OF THE INVENTION

Pursuant to this invention, hexafluorobenzene is converted to pentafluorobenzene magnesium bromide which is then reacted with a brominating agent, preferably elemental bromine to produce bromopentafluorobenzene. The bromopentafluorobenzene product may be used directly as an intermediate to synthesize metallocene olefin polymerization catalysts. Specifically, $C_6F_5MgBr$ is reacted with a halogenating agent to produce a halopentafluorobenzene which has the formula $C_6F_5X$, in which X is a halogen.

DETAILED DESCRIPTION OF THE INVENTION

In a first step, pentafluorophenyl magnesium bromide (Grignard) is prepared in known manner. See, e.g., Repress, et al. *J. Organometallic Chem.* (1969) 18:263–274 and Repress, et al., *J. Organometallic Chem.* (1969) 18:191–195 and U.S. Pat. No. 5,362,423.

In a second step, the $C_6F_5MgBr$ is quenched, preferably in the vessel in which it is produced by the addition of a halogenating agent in solution in non-interfering, preferably a hydrocarbon or chlorinated hydrocarbon solvent to produce a first reaction mixture containing bromopentafluorobenzene. Useful halogenating agents include elemental bromine, chlorine and iodine, carbon tetrachloride, carbon tetrabromate, chloroform, bromoform, and n-bromo or n-chloro succinamide. Elemental bromine is preferred.

Suitable solvents are straight or branched chain, five to ten carbon atom, aliphatic hydrocarbons, benzene, toluene, and two to ten carbon atom halogenated aliphatic hydrocarbons. Methylene chloride is preferred.

The halogenating agent is added in an amount at least stoichiometric with respect to the pentafluorophenyl magnesium bromide. Preferably, the halogenating agent is added in an amount within ninety (90%) percent of the stoichiometric amount.

The bromopentafluorobenzene so produced may be isolated in known manner and then reacted with a compound having the formula RLi, in which R is a straight or branched chain, saturated or unsaturated hydrocarbon group having two to ten carbon atoms, preferably n-butyl lithium, to produce pentafluorophenyl lithium, which in turn may be reacted with $BF_3$ or $BCl_3$ to produce tris(pentafluorophenyl) boron. Reaction of the tris(pentafluorophenyl) boron with pentafluorophenyl lithium produces tetrakis (pentafluorophenyl) borate.

EXAMPLE I

Procedure for Conversion of Hexafluorobenzene to Bromopentafluorobenzene

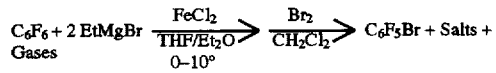

In a 2 l, $N_2$ purged flask were combined hexafluorobenzene (145 g), $FeCl_2$ (0.8 g) and THF (600 ml). The solution was cooled to 0°–5° C., and ethyl magnesium bromide (3.12M in $Et_2O$, 500 ml) was then added dropwise. After the addition was complete, the reaction mixture was stirred for one-half hour. A solution of bromine (125 g) n methylene chloride (250 ml) was then added dropwise to the cold (0°–5° C.) reaction mixture. After stirring 15 minutes, 4N HCl was added until all solids were dissolved. The two phases were separated and the organics were washed sequentially with water, aqueous sodium bicarbonate and brine. After drying over sodium sulfate, the mixture was distilled providing 160 g of $C_6F_5Br$ (83% yield).

The reaction mixture may also be reacted directly without isolation of the $C_6F_5Br$ with butyl lithium to produce $C_6F_5Li$ which, in turn, is reacted with $BCl_3$ or $BF_3$ to produce $(C_6F_5)_3B$.

I claim:

1. A method which comprises reacting $C_6F_5MgBr$ with a halogenating agent to produce a halopentafluorobenzene which has the formula $C_6F_5X$ in which X is a chlorine bromine or iodine.

2. The claim 1 method in which the halogenating agent is bromine, chlorine, iodine, carbon tetrachloride, carbon tetrabromide, chloroform, bromoform, or an n-bromo or n-chloro succinamide.

3. A method which comprises reacting $C_6F_5MgBr$ with bromine to produce bromopentafluorobenzene.

4. A method for converting hexafluorobenzene ($C_6F_6$) to bromopentafluorobenzene ($C_6F_5Br$) which comprises:
   (i) converting $C_6F_6$ to $C_6F_5MgBr$, and
   (ii) reacting said $C_6F_5MgBr$ of step (i) with a solution of bromine and a non-interfering solvent, to provide a reaction mixture containing bromopentafluorobenzene in solution in said solvent, and
   (iii) isolating said bromopentafluorobenzene from said step (ii) reaction mixture.

5. The claim 4 method in which said step (ii) non-interfering solvent is a 2 to 10 carbon atom hydrocarbon or a halogenated hydrocarbon.

6. The claim 4 method in which said non-interfering solvent is methylene chloride.

7. A method which comprises
   (i) reacting $C_6F_6$ with ethyl magnesium bromide in a medium comprising ethyl ether to produce $C_6F_5MgBr$ in solution in said medium;
   (ii) reacting said $C_6F_5MgBr$ with bromine in solution in methylene chloride, wherein $C_6F_5Br$ is produced.

8. The claim 7 method further comprising
   (iii) isolating said $C_6F_5Br$ produced in step (ii).

9. The claim 8 method further comprising:
   (iv) reacting said $C_6F_5Br$ isolated in step (iii) with n-butyl lithium to convert said $C_6F_5Br$ to $C_6F_5Li$.

* * * * *